United States Patent
Wissel et al.

(10) Patent No.: US 12,400,752 B2
(45) Date of Patent: Aug. 26, 2025

(54) IMAGE ANALYSIS METHOD AND DEVICE

(71) Applicant: KONINKLIJKE PHILIPS N.V., Eindhoven (NL)

(72) Inventors: Tobias Wissel, Lübeck (DE); Irina Waechter-Stehle, Hamburg (DE); Frank Michael Weber, Hamburg (DE); Arne Ewald, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 704 days.

(21) Appl. No.: 17/423,179

(22) PCT Filed: Dec. 30, 2019

(86) PCT No.: PCT/EP2019/087136
§ 371 (c)(1),
(2) Date: Jul. 15, 2021

(87) PCT Pub. No.: WO2020/148080
PCT Pub. Date: Jul. 23, 2020

(65) Prior Publication Data
US 2022/0130523 A1  Apr. 28, 2022

(30) Foreign Application Priority Data
Jan. 15, 2019 (EP) .................................. 19151746

(51) Int. Cl.
*G16H 30/40* (2018.01)
*G06N 20/00* (2019.01)
*G06T 7/00* (2017.01)
*G06T 7/11* (2017.01)
*G06T 7/136* (2017.01)
(Continued)

(52) U.S. Cl.
CPC ............. *G16H 30/40* (2018.01); *G06N 20/00* (2019.01); *G06T 7/0014* (2013.01); *G06T 7/11* (2017.01); *G06T 7/136* (2017.01); *G06T 7/143* (2017.01); *G06T 7/174* (2017.01); *G06T 2207/10132* (2013.01)

(58) Field of Classification Search
CPC ......... G16H 30/40; G06T 7/136; G06T 7/143; G06T 7/11; G06T 7/174; G06T 7/0014; G06N 20/00
See application file for complete search history.

(56) References Cited

U.S. PATENT DOCUMENTS

| | | | |
|---|---|---|---|
| 5,469,850 A | 11/1995 | Tizuka et al. | |
| 10,140,544 B1 * | 11/2018 | Zhao | ...................... G06N 20/00 |

(Continued)

OTHER PUBLICATIONS

International Search Report and Written Opinion of PCT/EP2019/087136, dated Feb. 13, 2020.
(Continued)

*Primary Examiner* — David Bilodeau

(57) ABSTRACT

An image analysis method and device is for detecting failure or error in an image segmentation procedure. The method comprises comparing (14) segmentation outcomes for two or more images, representative of a particular anatomical region at different respective time points, and identifying a degree of consistency or deviation between them. Based on this derived consistency or deviation measure, a measure of accuracy of the segmentation procedure is determined (16).

20 Claims, 2 Drawing Sheets

(a)

(b)

(c)

(51) Int. Cl.
  *G06T 7/143* (2017.01)
  *G06T 7/174* (2017.01)

(56) References Cited

U.S. PATENT DOCUMENTS

| | | | | |
|---|---|---|---|---|
| 2008/0205717 | A1* | 8/2008 | Reeves | G06T 11/008 382/128 |
| 2013/0182935 | A1 | 7/2013 | Wang et al. | |
| 2019/0188852 | A1* | 6/2019 | Reicher | G06T 7/0014 |
| 2020/0167930 | A1* | 5/2020 | Wang | G06N 3/08 |
| 2020/0401854 | A1* | 12/2020 | Peng | G06F 18/2148 |
| 2021/0383548 | A1* | 12/2021 | Wilson | G06T 7/0012 |

OTHER PUBLICATIONS

Jorgensen, Alex Skovsbo et al "An Improved Algorithm for Coronary Bypass Anastomosis Segmentation in Epicardial Ultrasound Sequences", Ultrasound in Medicine and Biology, vol. 42, No. 12, Sep. 2016, pp. 3010-3021.

Kirisli, H. et al "Evaluation of a Multi-Atlas Based Method for Segmentation of Cardiac CTA data: a Large-Scale, Multicenter, and Multivendor Study", Medical Physics, vol. 37, No. 12, Nov. 2010, pp. 6279-6291.

Li, Wei et al "Learning Image Context for Segmentation of the Prostate in CT-Guided Radiotherapy", Physics in Medicine and Biology, vol. 57, No. 5, Feb. 2012, pp. 1283-1308.

Ecabert, O. et al "Automatic Model-Based Segmentation of the Heart in CT Images" IEEE Transactions on Medical Imaging, vol. 27, No. 9, 2008, pp. 1189-1201.

Cortes, C. et al "Support-Vector Networks" Machine Learning, vol. 20, pp. 273-297, 1995.

Bishop, Christopher M. Neural Networks for pattern Recognition, Oxford Press, Inc. 1995.

Hautvast, G. et al "Validation of Automatic Segmentation Algorithms for SHort-Axis Cine Cardiac Magnetic Resonance", Proc. Intl. Society Mag. Reson. Med. vol. 15, 2007.

Barbosa, Daniel et al "Fast and Fully Automatic 3-D Echocardiographic Segmentation using B-Spline Explicit Active Surfaces: Feasibility Study and Validation in a Clinical Setting" Ultrasound in Medicine and Biology, vol. 39, No. 1, pp. 89-101, 2013.

Elen, An et al "A Spatio-Temporal Model for Joint Segmentation and Registration of Cardiac Cine MR Images" MICCAI 2010 Workshop.

Suri, J.S. et al."Greedy Algorithm for Error Correction in Automatically produced Boundaries form Low Contrast Ventrigulograms", Pattern Analysis and Applications, 2000.

* cited by examiner

IMAGE ANALYSIS METHOD AND DEVICE

CROSS-REFERENCE TO PRIOR APPLICATIONS

This application is the U.S. National Phase application under 35 U.S.C. § 371 of International Application No. PCT/EP2019/087136, filed on Dec. 30, 2019, which claims the benefit of European Patent Application No. 19151746.5, filed on Jan. 15, 2019. These applications are hereby incorporated by reference herein.

FIELD OF THE INVENTION

This invention relates to a method and device for analysis of images, in particular for assessing accuracy of segmentation procedures applied to images.

BACKGROUND OF THE INVENTION

Image segmentation is a procedure in digital image processing of partitioning a digital image into multiple segments (or groups of pixels), each covering some area or region of the image. It is most often used for locating objects and boundaries (e.g. lines, curves) in images. The different segments are typically identified and distinguished based on some similar shared graphical property of the pixels contained in that segmented region, e.g. color, intensity, or texture. Adjacent segmented regions will be different with respect to these same characteristic(s).

In the field of medical imaging, segmentation is valuable for identifying various anatomical structures or features within captured images such as for example organs, air and fluid passageways (such as blood vessels or digestive passages), valves, or chambers. The resulting contours after image segmentation enable more rapid assessment of medical images by clinicians (enabling quicker diagnosis or treatment decisions). The segmentation can also be useful for feeding in to subsequent processing techniques. For instance, a series or stack of images of a given region can be processed using the segmentation information to create a 3D reconstruction, for instance with the help of interpolation algorithms such as a Marching Cubes algorithm.

One important field of medical imaging is Ultrasound. Ultrasound plays an important role in assessment and diagnosis for a wide range of areas of the body. Its use in cardiac imaging in particular is highly valuable.

Diagnosis, treatment and planning are often based on utilizing a clear delineation of relevant anatomical sites or features within ultrasound images. In the field of cardiac imaging for instance, these sites may include the ventricles, the atria or surrounding vessels. Segmentation is frequently used to automate this delineation process.

Many organs or anatomical objects in the body undergo cyclical movement patterns, for instance the movement of the heart and its internal chambers during the heart cycle (cycle between systole and diastole as the heart beats) or for instance the contraction and expansion of the lungs during the breathing cycle.

Model-based image segmentation is often used for medical imaging. Model based segmentation uses pre-determined models, for instance of a particular anatomical region, which models typical shapes, sizes, textures or other graphical features characteristic of certain anatomical structures or features. These model properties can be imposed as constraints on the segmentation, e.g. wherein the model is fitted to the imaging data, to thereby enable segmentation of anatomical features.

Despite improvements, image segmentation is frequently unreliable. Due to poor image quality, anatomical anomalies, or an unexpected imaging field-of-view for example, the automatic delineation of structures can frequently fail. Failure of the segmentation process can be for a number of reasons. For instance the algorithm may misinterpret the input image content, or the images may lack sufficient resolution or signal content in certain areas to enable accurate delineation of boundaries and lines. For example, the model based segmentation relies on assessing image features such as gradients or textures. Poor ultrasound signal quality or missing signal data in certain anatomical regions can lead to failure of the procedure. This can lead to inaccurate delineation of image features and therefore unreliable segmentation results.

More particularly, failure to accurately identify the underlying image properties or features (i.e. properties of the pixels) can lead to incorrect fitting (or adaptation) of the model to the image. This results in inaccurate and inconsistent segmentation results.

Failures in the segmentation procedure may manifest in the segmentation outcome in the form of unrealistic distortions of the model shape, but also model shapes which appear plausible but which in fact deviate significantly from the true underlying anatomy.

Detecting when segmentation has failed is extremely important to avoid clinicians basing medical judgments on inaccurate segmentation results. This is most important when the failed segmentation outcome nonetheless appears plausible in shape.

The typical approach to detecting segmentation failure in the state of the art is to compare the segmentation results with the underlying image to look for characteristic irregularities which are indicative of failure. However this approach is very challenging. In particular, many segmentation failures occur due to poor quality or missing signal data in certain areas. These same areas of low signal often also lead to similar errors being made by the checking algorithm itself, which may lead to ambiguity as to what represents a successful result and what represents a failed result.

An improved approach to detecting segmentation errors would therefore be of value.

The paper JORGENSEN ALEX SKOVSBO ET AL: "An Improved Algorithm for Coronary Bypass Anastomosis Segmentation in Epicardial Ultrasound Sequences", ULTRASOUND IN MEDICINE AND BIOLOGY, vol. 42, no. 12, pages 3010-3021, relates to a method for automatically segmenting coronary bypass anastomoses within in vivo endoscopic ultrasound (EUS) sequences. In particular, an automatic anastomosis segmentation algorithm is used to extract the area of anastomotic structures from in vivo EUS sequences obtained from 16 porcine anastomoses. The algorithm consists of four major components: vessel detection, vessel segmentation, segmentation quality control and interframe contour alignment. The segmentation accuracy is assessed using m-fold cross-validation based on 830 manual segmentations of the anastomotic structures.

The paper K1 RIAA LI H ET AL: "Evaluation of a multi-atlas based method for segmentation of cardiac CTA data: a large-scale, multicenter, and multivendor study", MEDICAL PHYSICS, AIP, MELVILLE, NY, US, vol. 37, no. 12, 18 Nov. 2010, pages 6279-6291, relates to a method for segmenting cardiac computed tomography angiography (CTA) data. In particular, an automatic multiatlas based method for segmenting the whole heart (i.e., the outer surface of the pericardium) and cardiac chambers from CTA data is discussed. In the segmentation approach, eight atlas images are registered to a new patient's CTA scan. The eight corresponding manually labeled images are then propagated and combined using a per voxel majority voting procedure, to obtain a cardiac segmentation.

The paper WEI LI ET AL: "Learning image context for segmentation of the prostate in CT-guided radiotherapy", PHYSICS IN MEDICINE AND BIOLOGY, INSTITUTE OF PHYSICS PUBLISHING, BRISTOL GB, vol. 57, no. 5, 17 Feb. 2012, pages 1283-1308, relates to a method of segmenting the prostate in CT images based on use of classifier algorithms, where the classifiers are updated or trained with each newly derived segmentation result. In particular, an online-learning and patient-specific classification method is presented. Two sets of location-adaptive classifiers are placed, respectively, along the two coordinate directions of the planning image space of a patient, and further trained with the planning image and also the previous-segmented treatment images of the same patient. Each location-adaptive classifier is recursively trained with both the static image appearance features and the iteratively updated image context features.

SUMMARY OF THE INVENTION

The invention is defined by the claims.

According to examples in accordance with an aspect of the invention, there is provided an image analysis method for determining failures in an image segmentation procedure, where the segmentation procedure is for identifying and segmenting one or more anatomical features in an image, and the method comprising:

obtaining image segmentations of two or more images of an anatomical region, representative of the region at different respective time points, and each segmented using said segmentation procedure;

comparing one or more similar segmented features, segmented in each of the image segmentations, and deriving one or more measures of consistency between the features in the different segmentations; and determining a measure of accuracy of the segmentation procedure based on the one or more consistency measures.

The method is for example a computer implemented method.

The invention is based on the insight that failures in segmentation algorithms are highly sensitive to small changes in the input data. This has been found to manifest in large variation in segmentation outcomes for images taken at different times (where imaging conditions, such as probe position may be slightly different for instance). It has therefore been realised that failed segmentation might be detected by looking for such variation. Hence, the invention proposes comparing segmentation results for images taken at multiple different time points of the same anatomical region, to thereby enable faults in the segmentation algorithm to be detected.

This approach is perfectly suited to medical imaging, where it is very common to capture a time-series of images of the same region as part of the examination. The accuracy checking procedure of the invention hence fits naturally into the normal workflow of the medical imaging.

The approach differs to known approaches in that it is based on comparing the outcomes of the segmentation algorithm with each other, rather than only comparing each segmentation outcome with the underlying image on which it is based. This hence avoids the problems associated with known accuracy checking procedures.

The image segmentations are for example segmentations of two or more images of an anatomical region of a single patient.

The segmentation procedure is for example an automated segmentation procedure, for example involving one or more segmentation algorithms.

As noted, the large variation as a function of time arises due to high sensitivity of typical segmentation errors to even small changes in input data. Some example input data changes which can lead to large changes in output segmentation results include for instance movement of the ultrasound transducer unit (e.g. probe) when acquiring the data, changes in the (speckle) noise pattern, or anatomical motion over time.

The different time points may be some minimum separation from one another in time. This may help ensure that imaging conditions have changed sufficiently to lead to variation in the segmentation outcome.

Variation in the segmentation results may be detected via measuring consistency between segmented anatomical features in the segmentation. This can be based on determining a measure of consistency in one or more (e.g. spatial or geometrical) properties of the segmented anatomical features, e.g. size, shape, position.

A single measure of consistency may be derived representative of an overall consistency between two or more segmentations, with the segmentations taken and compared as a whole.

In other examples, consistency measures may be derived based on assessing consistency between individual segmented (anatomical) features of the segmentations. Multiple measures of consistency may be derived corresponding to the different compared features in some examples. In other examples, a single measure of consistency may be derived, representative of an overall, e.g. average, consistency of a whole set of segmented anatomical features. In other examples, a respective measure of consistency may be derived for each of the segmented anatomical features, i.e. a separate measure of consistency for each of the segmented features.

The consistency measures can be defined in different ways. They may in some examples be defined in terms of a measure of deviation between one or more segmented features (e.g. between one or more properties of segmented features).

The segmented features may refer in practice for instance to segmentation outlines or boundaries intended to correspond to anatomical features of the underlying image.

The image segmentations are the outcomes or results of application of the segmentation procedure. The segmentation procedure means an automated segmentation procedure, for example based on one or more segmentation algorithms. The segmentations may take a variety of forms.

In certain cases, the image segmentation may comprise a segmentation mesh for application to the image, or applied to the image. In an accurately segmented image, the segmentation mesh feature outlines should match up with the actual anatomical features in the image.

The segmentation may instead take the form of a set of boundary outlines of different anatomical features. The segmentation may take the form of a set of data classifying each pixel in the image in terms of the anatomical structure within which it falls in the image. The segmentation can hence in general be represented graphically or simply with (e.g. non-graphical) segmentation data.

In some cases, the segmentation may include both the segmentation outcome and the underlying image, e.g. one overlaid atop the other.

In examples, one segmentation of each of the two or more images may be obtained, i.e. there are obtained respective segmentations of each of the two or more images.

The measure of accuracy indicates how reflective of the true anatomy the segmentation is. This may in examples be a quantitative measure, e.g. indicative of a degree of accuracy. It may be a binary measure, e.g. accurate or not accurate. It may be a probabilistic measure, i.e. indicative of a likelihood that the segmentation is accurate.

According to examples, the method may further comprise generating a data output representative of the measure of accuracy. The method may further include communicating said data output to an external device, such as a remote computer or server.

Any embodiment of the method may be implemented by a computer or processor or controller in examples.

As noted above, according to one or more examples, the comparing of the image segmentations and/or deriving of the one or more measures of consistency may comprise comparing one or more similar segmented features, segmented in each of the image segmentations, and deriving one or more measures of consistency between the features in the different segmentations.

The measure of accuracy may in some examples be determined based on applying one or more pre-determined minimum thresholds for the consistency measure(s).

The measure of accuracy may be determined based on the one or more derived measures of consistency and on reference to a pre-determined normal degree of inconsistency between the image segmentations for images captured at said different time points.

For instance, where minimum thresholds are applied as noted above, these thresholds may represent some expected normal level of variation in the segmented feature, due to changes in the underlying anatomy as a function of time. Hence, the one or more minimum thresholds may be representative of a pre-determined expected (or normal) degree of inconsistency between the respective segmented features for images captured at said different time points.

More generally, reference to a normal degree of inconsistency allows for measured or derived inconsistency between segmentations to be calibrated against the expected inconsistency due to anatomical changes.

The aim is to detect abnormal changes in the segmentation, deviating from expected or plausible variations in the actual anatomy. This ensures that variations due to actual anatomical movements are not mistaken for segmentation errors.

These expected levels of inconsistency may be due to variations or movement in the underlying anatomy, or simply due to expected (but tolerable) random variation in segmentation results.

Here, the procedure for determining the measure of accuracy may for instance take into account expected (normal) changes in the size, shape, position of one or more features in the underlying anatomy as a function of time for instance.

Where thresholds are used, different pre-determined thresholds for the one or more consistency measures may be used depending upon the particular segmented features which the consistency measures relate to, i.e. the threshold applied may vary in dependence upon the anatomical features in question.

According to an advantageous set of embodiments, the deriving the one or more measures of consistency and/or the deriving the measure of accuracy may be based on use of machine learning algorithm.

The algorithm may in examples be trained for distinguishing between normal and abnormal levels of inconsistency between image segmentations of the anatomical region representative of the region at said different time points. The algorithm may be configured to compare image segmentations, taking into account normal expected levels of inconsistency, and to derive the one or more measures of consistency. The algorithm preferably also determines the overall measure of accuracy. The deriving of the one or more measures of consistency and the measure of accuracy may be performed as a singled integrated procedure by the machine learning algorithm in some examples.

Where thresholds are used for deriving the consistency measure, the one or more pre-determined thresholds for the consistency measure(s) may be embodied by the machine learning algorithm. The machine learning algorithm may hence in some cases be understood as performing the role of a set of thresholds, via the algorithmic process which it applies.

One approach to taking into account the expected normal variation due to anatomical changes is to include, as discussed above, a pre-stored set of minimum thresholds for the consistency measures, with the levels of these set to be above the level of normal anatomical variations. One threshold may be included for each feature or each portion of a feature for instance.

However, it may be computationally more efficient to apply new developments in the field of machine learning, to enable use of a classifier algorithm, trained using prior data representative of both accurate and non-accurate segmentations of the anatomical region.

A machine learning algorithm may be able to take a more holistic approach to the assessment, considering the segmentations as a whole and comparing them to one another, rather than applying individual thresholds to individual features. This may lead to more accurate results, for instance certain nuances which arise when considering interaction between segmented anatomical features over time may be more effectively taken into account.

The machine learning algorithm may perform both the comparison step and the accuracy determination step. The processes of deriving the measure of consistency between the segmentations and of the measure of accuracy may both be integrally embodied in the overall classification procedure performed by the algorithm, The machine learning algorithm may employ a neural network in examples.

More broadly, a classifier algorithm may be used adapted to determine the consistency measure based on comparing the multiple segmentations with one another (and then classifying the segmentation outcomes as accurate or non-accurate accordingly). The classifier algorithm may employ machine learning or deep learning using training data as discussed above.

According to one or more examples, the measure of accuracy may comprise a probabilistic measure of accuracy, i.e. representative of a probability of accuracy.

Embodiments of the invention comprise determining a measure of consistency between different segmentations. This may mean for instance a measure of consistency between one or more segmented anatomical features within the image segmentations, for instance between one or more properties of different segmented features. These may include shape, position and/or size properties for instance.

Hence, according to one or more embodiments, determining the one or more measures of consistency for the segmented features may comprise comparison of a position, shape, and/or dimensions of at least a portion of an outline of each of the features (e.g. within the image segmentation).

According to an advantageous set of embodiments, the different time points may correspond to defined time points in a periodic or cyclic movement pattern of the imaged anatomical region, e.g. different points in a heart cycle (e.g. end-systole and end-diastole), or different points during a breathing cycle.

This may allow for uniformity or consistency in the derived consistency or accuracy measures, since the segmentations being compared are representative of the same set of anatomical time points. At these time points, the anatomy can be expected to have changed by some standard definable amount.

According to certain examples, the method may comprise both obtaining the image segmentations and obtaining the images upon which the segmentations are based.

According to one or more sets of embodiments, the method may be performed in real time with the obtaining of said image segmentations.

In some examples, the method may be performed in real time with acquisition of image data representative of the region, for example wherein the method comprises processing said received image data to thereby obtain the two or more image segmentations.

The method may comprise receiving or acquiring a series of images or segmented images and performing the method in real time with their acquisition for instance. The method may comprise controlling an associated ultrasound transducer unit to acquire one or more images, and performing the method in real time with their acquisition. This may include applying a segmentation algorithm to said acquired images.

In a certain set of embodiments, the method may be an ultrasound image analysis method. Here, the method is for use with (i.e. for analyzing) ultrasound images; the images analyzed are ultrasound images.

The image segmentations can be obtained in different ways. In some examples, the image segmentations may be received, for instance, from an external ultrasound imaging unit, or from an ultrasound transducer unit.

The obtaining of the one or more image segmentations may comprise receiving one or more images and processing the images with the segmentation procedure.

The obtaining the one or more image segmentations may comprise receiving ultrasound data, processing the data to derive a set of two or more images, representative of the anatomical region at different respective time points, and processing the derived one or more images with the segmentation procedure.

Examples in accordance with a further aspect of the invention provide an image analysis device for determining failures in an image segmentation procedure, where the segmentation procedure is for identifying and segmenting one or more anatomical features in an image, the device comprising:

an acquisition module configured to obtain image segmentations of two or more images of an anatomical region, representative of the region at different time points, and each segmented using said segmentation procedure;

a comparison module configured to compare the image segmentations, and to derive one or more measures of consistency between the different segmentations; and an analysis module configured to determine a measure of accuracy of the segmentation procedure based on the one or more consistency measures.

Implementation options and details for each of the above features may be understood and interpreted in accordance with the explanations and descriptions provided above for the method aspect of the present invention.

Any of the examples, options or embodiment features or details described above in respect of the method aspect of this invention may be applied or combined or incorporated mutatis mutandis into the present apparatus aspect of the invention.

Examples in accordance with a further aspect of the invention provide an ultrasound system, comprising: an ultrasound transducer unit; and an image analysis device in accordance with any example or embodiment outlined above or described below, or in accordance with any claim of this application, operatively coupled with the ultrasound transducer unit for use in obtaining said two or more image segmentations.

In examples, the image analysis device may be configured to control the ultrasound transducer unit to acquire the two or more images of said anatomical region for segmentation.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an image analysis method and device for detecting failure or error in an image segmentation procedure. The method comprises comparing segmentation outcomes for two or more images, representative of a particular anatomical region at different respective time points, and identifying a degree of consistency or deviation between them. Based on this derived consistency or deviation measure, a measure of accuracy of the segmentation procedure can be determined.

For example, image segmentation sets which fail to meet some minimum similarity threshold, or plurality of thresholds (for different segmented features for instance) may be determined be inaccurate or have a low level of accuracy.

Hence, the invention proposes to identify failures in a segmentation algorithm based on consistency checks between segmentations for different images taken of the same anatomical region at different times.

A typical characteristic of segmentation failures is a high sensitivity to small changes in the input image data, particularly background patterns or features which are not representative of changes in the actual objects being imaged. The effect of this is that different segmentation outcomes may all fail, but the manner in which that failure is manifested in the final segmentation may change by a large degree. During an acquisition, common variations in the input data which may lead to these segmentation variations include, for instance, probe motion, or changes in the (speckle) noise pattern.

Since segmentation failures are sensitive to these changes in the input data, natural variations in the data over a sequence of acquired images will have a substantial effect on their appearance.

Given at least two image-segmentations, consistency measures can be computed. These consistency measures may be quantitative, e.g. defined along a spectrum or scale of consistency. The consistency measures may be binary, e.g. classifying the compared segmentations into normal (corresponds to segmentation success) and abnormal (corresponds to segmentation failure). The method is not restricted to use of only two segmentations and use of a greater number of segmentations may increase the accuracy of results.

In some examples, the corresponding images for each segmentation may be acquired and utilized in addition to the image segmentations themselves. The two may be combined or superposed with one another in some examples (e.g. with segmentation boundaries superposed atop each respective image).

Having the images in addition to the segmentations is an optional additional feature, allowing a greater number of features or details can be extracted in the comparison procedure than with the segmentations alone. For example, the image data may enable image intensity (e.g. for different segmented features) to be taken into account in comparisons between segmentations.

Figure 1:
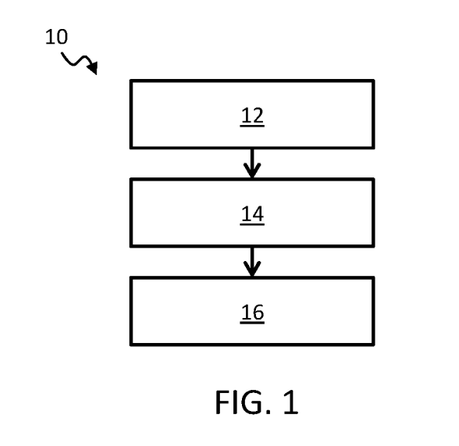
FIG. 1 shows in block diagram form an example method according to one or more embodiments.

A first, simple example of an image analysis method according to one or more embodiments is shown in block diagram form in FIG. 1. The method 10 is for determining failures in an image segmentation procedure, where the segmentation procedure is for identifying and segmenting one or more anatomical features in an image.

In brief, the method 10 comprises obtaining 12 image segmentations of two or more images of an anatomical region, representative of the region at different respective time points, and each segmented using said segmentation procedure.

The method further comprises comparing the image segmentations, and deriving 14 a measure of consistency between the different segmentations. For example, one or more similar segmented features, segmented in each of the image segmentations, may be compared in some examples, and a measure of consistency between the features in the different segmentations derived.

The method further comprises determining 16 a measure of accuracy of the segmentation procedure based on the one or more consistency measures.

According to certain particular examples, in cases when imaging a moving object (e.g. an object such as the heart or lungs which is cyclically varying), the deriving of the consistency measure(s) may take into account an expected normal degree of variation in the segmentations due to underlying changes in the anatomy.

In particular, if normal or plausible changes of the segmented anatomy such as typical probe or heart motion can be described and encoded, abnormal variations can be detected. By way of example, for heart segmentation, knowledge of the particular point in the cardiac cycle at which an image is taken permits a great deal of information about the current state of the anatomy to be estimated. The relative change in the anatomy between two known points can also be estimated. In the context of cardiac imaging for instance, it is common to capture ultrasound images representative of the heart at the end diastole (ED) time point in the heart cycle and at the end-systole (ES) time point.

The method comprises obtaining 12 segmentations of at least two images (i.e. a plurality of images), representative of the anatomical region at different respective times. The two images may be images captured in temporal sequence during a single imaging session, or may be captured in different imaging sessions. The images are preferably recorded in the same coordinate system.

Obtaining 12 the one or more image segmentations may comprise receiving the segmentations pre-formed or pre-computed from an external source, for example from an external ultrasound imaging unit, or from an ultrasound transducer unit, or for instance from a memory or data-store (where the method is being used for post-processing and images and segmentations have already been derived for instance).

In some examples for instance, imaging data from a plurality of past examinations for a given patient may be accessed or acquired from a data-store. A current or most recent set of acquired image data may be compared with the stored past data for the previous examinations, and the one or more measures of consistency derived with respect to segmentations of images from the previous examinations.

In these examples, it may be advantageous to store and utilize additional image intensity information (e.g. based on storing the image data as well as the derived segmentations), since comparisons outside the same temporal sequence (i.e. outside the same single imaging session) may exhibit variations due to varying transducer positions or different patient health states (i.e. variations not related to segmentation accuracy).

In other examples, obtaining 12 the one or more image segmentations may comprise receiving one or more images and processing the images with the segmentation procedure.

In examples for instance the method may comprise receiving a sequence of input images, representative of a given anatomical region at different time points. The method may comprise processing the images with a segmentation procedure. This may be implemented for instance using a dedicated segmentation module or otherwise.

The segmentation procedures may provide, as an output, segmentations of the anatomy of interest for each image.

The image segmentation is preferably anatomical model based segmentation, which employs models of the anatomical region being imaged to assist in identifying the important anatomical features or objects.

Model-based image segmentation in the field of medical imaging is a well-known procedure and the skilled person will be aware of various example segmentation algorithms which may be employed to implement the image segmentation.

By way of one example, a suitable example segmentation algorithm which may be employed in embodiments is described in detail in the paper: Ecabert, O et al. Automatic Model-Based Segmentation of the Heart in CT Images Medical Imaging, IEEE Transactions on, 2008, 27, pp. 1189-1201.

Different segmentation algorithms may be employed for segmenting images of different anatomical regions, e.g. the heart, lungs, digestive tract, neck, groin or any other region.

According to certain examples, a reduced or simplified version of the segmentation procedure may be employed in some instances. This may be useful for instance in time-constrained applications (for instance where the method is being run in real time with image acquisition during an examination), where there is insufficient time, given constraints on processing power, to apply the full model to all of the images in the received series (for instance to both the end-diastole and the end-systole image frame where the series consists of these heart cycle time points).

The simplified or reduced version of the segmentation procedure may be a faster, auxiliary model, pared back in certain respects. This auxiliary model may produce lower resolution results, but wherein the derived distinctions between different segments (e.g. the derived boundary geometries and positions) are unchanged compared to the full model. Hence the auxiliary mode may still share the fundamental image feature recognition properties as the full segmentation model, to ensure that failures occur in the same way as for the full model.

By way of example, considering for instance model-based segmentation (such as that outlined in the example paper above), a reduced version of the model may be obtained by reducing triangle resolution in the model's mesh representation, reducing the number of iterations in the adaptation process, dropping analysis of more detailed anatomical structures such as pulmonary veins, or any other suitable adaptations for instance which relate to non-essential features of the segmentation.

In deep-learning based segmentation approaches, a reduced deep-learning model may be achieved for instance by reducing the network's depth, reducing input image size (by e.g. down-sampling), or any other suitable modification.

In certain cases, the image segmentation outcome may comprise a segmentation mesh describing or representative of the anatomical information contained in the input image. The mesh may be applied to the image in some cases. In an accurately segmented image, the segmentation mesh feature outlines should match up with the actual anatomical features in the image.

The segmentation may instead take the form of a set of boundary outlines of different anatomical features. The segmentation may take the form of a set of data classifying each pixel in the image in terms of the anatomical structure within which it falls in the image. The segmentation can hence in general be represented graphically or simply with (e.g. non-graphical) segmentation data.

In some cases, the segmentation may include both the segmentation outcome and the underlying image, e.g. one overlaid atop the other.

The output segmentation comprises identification of various anatomical features, which may include anatomical objects such as organs, chambers, valves, blood or air passageways, or may include any portion or section of such objects, e.g. an apex of the left ventricle.

The segmentation may identify outlines or boundaries of such features for example, or an area over which they extend for instance.

The segmentation output, e.g. meshes, for each of the two or more images (e.g. from the ED and the ES cardiac phase in the case of cardiac imaging) provide an indication of the characteristic segmented anatomical features for each segmentation. Changes in these features between the different image segmentations may be detected and a measure of consistency between the respective features, or between the segmentations as a whole, derived based on this.

By way of example, the consistency measures between the segmentations may correspond to measures of consistency between one or more properties of one or more different segmented features. These may include for instance shape, position and/or size properties for instance.

Determining the measure of consistency may hence comprise comparison of a position, shape, and/or dimensions of at least a portion of an outline of each of a set of one or more segmented anatomical features.

Examples of properties of segmented anatomical features which may be compared to derive the one or more measures of consistency include for instance the overall height of the left heart side, height and width of the left ventricle, motion of the upper tip of the left atrium, the apex, right ventricle lateral wall and the ventricular septum between ED and ES phase. These represent illustrative examples only, and numerous other potential properties exist whose variations may be used as a basis for deriving the consistency measures between the segmentations or between the segmented features of the segmentations.

Figure 2:
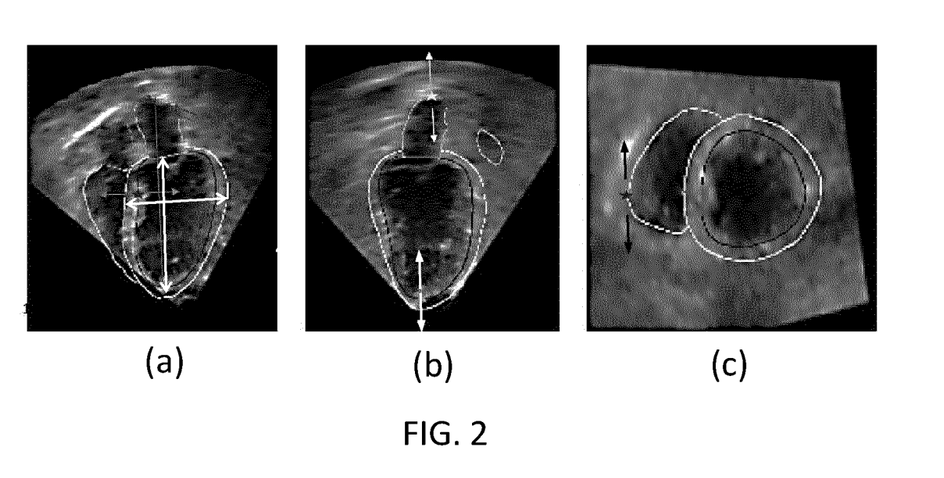
FIG. 2 illustrates determination of example consistency measures between example segmented features in different segmentations.

FIG. 2 illustrates changes in some example anatomical feature properties which may be used for determining the measures of consistency between the anatomical features in the different segmentations.

FIG. 2(a) shows an ultrasound image of a subject's heart. For purposes of illustration, two segmentations are shown superposed, corresponding to images of the heart at different times. White arrows illustrate height and width of the left ventricle. Changes in height and/or width may be used for determining the consistency measure(s). An additional property whose variation may be detected may be for instance the overall height of the heart region.

FIG. 2(b) illustrates, as another possible property which may be used to determine consistency measures, the position of the upper tip of the left atrium (show at the top of the heart) and the position of the heart apex (shown at the bottom of the heart). White arrows schematically illustrate motion of these points which may occur between different segmentations for images corresponding to different time points.

FIG. 2(c) illustrates by way of example movement of the right ventricle lateral wall. FIG. 2(c) shows a view of the heart across a plane perpendicular to the heart height. The black arrow illustrates schematically the example motion.

In some examples, the derived changes in one or more of position, size or shape properties of the segmented features may be used directly as the consistency measures between the segmentations. These may for instance be fed to an algorithm (for instance a classifier algorithm) for determining the measure of accuracy of the segmentation procedure.

In other examples, the derived changes in the one or more of position, size or shape properties of the segmented features may be further processed to derive the one or more measures of consistency. For instance, an average of one or more of the property changes may be taken, or the property changes may be combined in any other way.

Using the derived one or more consistency measures, a measure of accuracy of the segmentation is determined 16.

According to one or more embodiments, this may comprise applying to the consistency measures a set of minimum consistency thresholds, these representative of an expected maximum level of normal background variation.

In cases when imaging a moving object (e.g. cyclically varying), these thresholds may take into account an expected normal degree of variation in the segmentation features due to underlying changes in the anatomy.

Hence, in examples, the one or more minimum thresholds may be representative of a pre-determined normal degree of inconsistency between the segmentations, e.g. between respective segmented features (or different properties of those features) for images captured at said different time points.

According to an advantageous set of embodiments, a classification algorithm may be employed for determining the measure of accuracy, which may advantageously be a machine learning or deep learning algorithm, for instance employing a neural network.

A machine learning algorithm may be trained for distinguishing between normal and abnormal levels of inconsistency between image segmentations of the anatomical region representative of the region at said different time points.

Based on the derived set of one or more consistency measures, the classification algorithm determines an accuracy measure, e.g. distinguishes between accurate and inaccurate segmentation.

The measure of accuracy may be quantitative, e.g. a value along a spectrum or scale of accuracy. The measure of accuracy may be binary, e.g. accurate or not accurate. The measure of accuracy may according to one to one or more examples be a probabilistic measure of accuracy.

As noted, a classification algorithm may be a machine learning algorithm. One example type of machine learning algorithm which might be employed is a support vector machine. Details for implementation of such an algorithm are outlined for instance in the paper: C. Cortes, V. Vapnik, Support-vector networks, Machine Learning, 20, 273-297 (1995).

Another example type of machine learning algorithm which might be employed is a neural network based algorithm. Further details on implementation of such an algorithm are outlined for example in the paper: Christopher M. Bishop. Neural Networks for Pattern Recognition. Oxford University Press, Inc., New York, NY, USA. 1995.

According to examples, where a machine learning classifier algorithm is used for determining the measure of accuracy, this algorithm may be first trained using sample consistency measures extracted from a set of reference data. This training may be included as an optional initial step in the method in certain embodiments. The training step may be performed only once, with the remaining steps 12, 14, 16 then performed as many times as required for different sets of image segmentations.

By way of examples, the algorithm may be trained using example segmentations produced by both an accurate segmentation procedure and an inaccurate segmentation procedure. The algorithm may therefore model typical patterns for the purpose of subsequently distinguishing between successful and unsuccessful segmentations.

For example, the algorithm may learn to distinguish normal levels and types of variation between segmentations, e.g. segmented features in the segmentations, and abnormal levels and types.

An example procedure for training a machine learning classifier algorithm for determining the measure of accuracy of the segmentation procedure will now be described.

A set of training data may be prepared or provided, wherein each case in the training data is labeled (e.g. by a human expert) as either representative of a failed or successful segmentation (an accurate or inaccurate segmentation procedure).

During training of the classifier algorithm, the classifier algorithm parameters are optimized with respect to the training data such that it successfully recognizes and distinguishes normal variation (i.e. representative of accurate segmentation results), and also unusual variation (i.e. representative of inaccurate segmentation results).

The algorithm may in some examples be trained to provide results as a two-class output, meaning that it can separately identify accurate segmentation results and inaccurate segmentation results. In this example, the algorithm is trained with examples of both accurate and inaccurate (i.e. successful and unsuccessful) segmentation results. When forming an accuracy determination, the algorithm may look for properties in the segmentations which it has learned as being indicative of accurate segmentation and which it has learned as being indicative of inaccurate segmentations.

Alternatively, the algorithm can be trained in terms of a one-class problem, wherein the algorithm is trained merely to detect anomaly or deviation from some normal population of sample data. Hence here the algorithm may be trained using only examples of segmentations produced by accurate segmentation procedures. The algorithm may then detect whether a new segmentation is inside or outside the modeled population of accurate cases which it has learned.

As noted above, one example machine learning classifier algorithm which may be employed is a support vector machine. Such an algorithm learns weights for kernel evaluations (similarities) between test and training samples.

Another example is a neural network. A neural network receives inputs/features of the input and computes a weighted sum of these, which is then passed through a function, the function typically being a non-linear function. This process may be performed in each of a plurality of layers of the neural network, where the number of layers is typically referred to as depth of the network.

A simple example case may be logistic regression. Here, the output of the algorithm is probabilistic, and outputs a value between 0 and 1, indicating a likelihood that a segmentation procedure is accurate.

In examples, the training procedure may also include providing to the algorithm as part of the training data the underlying image data.

According to one or more examples, the method may include a further step of generating a data output representative of the derived measure of accuracy of the segmentation procedure.

In certain examples, the method may comprise generating an output for providing to an associated user interface for communicating the derived accuracy measure to the user interface. This may be a control output for instance for controlling the user interface to generate a sensory output representative of the derived accuracy measure, for instance for controlling a display of the user interface to display the measure.

The user interface may hence notify a user of a problem with the segmentation algorithm, and may be configured to determine suggestions for changes in an image acquisition procedure.

For example, the interface may display information indicating properties or aspects of the input data which are leading to poor segmentation results, and may provide recommendations for changes in the data acquisition method for remedying the segmentation errors. In some examples, the system may be adapted to automatically switch to a semi-automatic mode of data acquisition, to avoid continuance of data acquisition errors.

According to certain examples, the method may apply a filtering process whereby only segmentations whose assessment leads to an acceptable accuracy measure are displayed or used.

In accordance with a further aspect of the invention, an image analysis device may be provided which is configured to perform any example or embodiment of the above described method outlined in this disclosure, or in any claim.

Accordingly, examples provide an image analysis device for determining failures in an image segmentation procedure. An example image analysis device 30 according to one or more embodiments is shown in block diagram form in FIG. 3.

Figure 3:
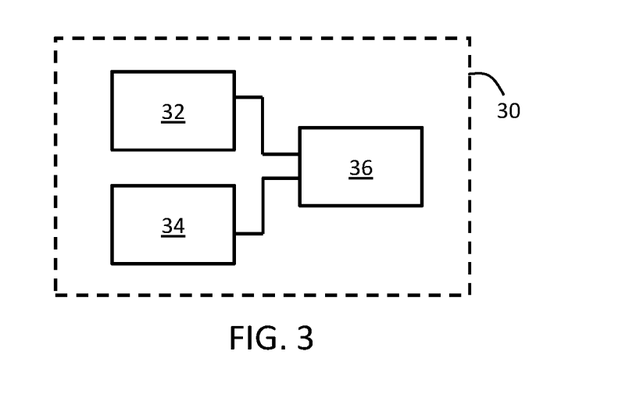
FIG. 3 shows in block diagram from an example image analysis device according to one or more embodiments.

The device comprises an acquisition module 32 configured to obtain image segmentations of two or more images of an anatomical region, representative of the region at different time points, and each segmented using said segmentation procedure.

The device further comprises a comparison module 34 configured to compare the image segmentations, and deriving a measure of consistency between the different segmentations.

The device further comprises an analysis module 36 configured to determine a measure of accuracy of the segmentation procedure based on the one or more consistency measures.

Implementation options and details for each of the features of the above device may be understood and interpreted in accordance with the explanations and descriptions provided above in respect of the method aspect of the invention.

Any of the examples, options or embodiment features or details described above in respect of the method may be applied or combined or incorporated mutatis mutandis into the present device aspect of the invention.

It is noted that although in the above example, the acquisition module 32, comparison module 34 and analysis module 36 are shown as separate components within the image analysis device 30, this is not essential. Their relevant functionalities may be distributed in different ways among one or more components. In some examples for instance, the functionality of the different modules may be integrated and performed by a single element, for example by a single controller or processor, or their functionalities may be otherwise distributed between one or more elements or components. Alternatively, the functionality of each module may be performed by a separate controller or processor within the image analysis device.

The device, according to one or more embodiments, further comprise a user interface for communicating the derived measure(s) of accuracy to a user, for instance by generating a sensory output representative of the measure(s).

The user interface may comprise a display for generating a visual output representative of the derived accuracy measure(s).

The functionality of one or more of the above modules may be implemented by a controller or processor. A separate controller or processor may be provided for implementing the functionality of each respective module or the functionality of all of the modules may be performed by a single controller or processor.

A controller may be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

A further aspect of the invention provides an ultrasound system. An example ultrasound system is shown in block diagram form in FIG. 4. The system 40 comprises: an ultrasound transducer unit 38; and an image analysis device 30 in accordance with any example or embodiment outlined above or described below, or in accordance with any claim of this application, operatively coupled with the ultrasound transducer unit for use in obtaining said two or more image segmentations.

Figure 4:
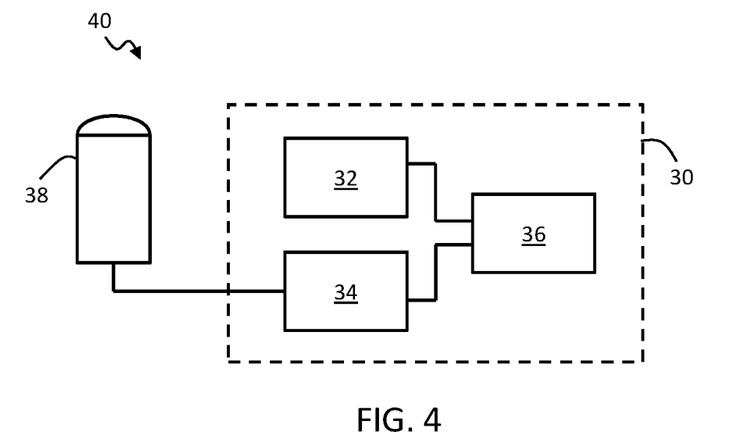
FIG. 4 shows in block diagram form an example ultrasound system comprising an example image analysis device according to one or more embodiments.

The ultrasound transducer unit 38 may provide ultrasound image data to the image analysis device 30 and the image analysis device may be adapted to process this data with the segmentation algorithm to derive the two or more segmentations.

The image analysis device 30 may be adapted to control the ultrasound transducer unit 38 to acquire ultrasound image data.

The ultrasound transducer unit 38 may take any suitable form, for instance an ultrasound probe, or an ultrasound sensor with a flat form factor. The transducer unit comprises one or more ultrasound transducers, for instance an ultrasound transducer array.

Embodiments of the present invention may be applied in any context in which segmentation is applied to medical images. A particularly valuable area of application is ultrasound imaging, for instance ultrasound imaging of the heart area.

The system, method or device of the invention may be configured for real-time assessment of segmentation accuracy. It may advantageously be implemented as part of an ultrasound unit such as a ultrasound workstations to provide analysis results in real time with image data acquisition.

As noted, although some examples have been described above with reference to application of the invention to imaging of the heart region, the invention is not restricted to use for cardiac imaging, and can be used for segmentations of images of any anatomical region.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. An image analysis method for determining failures in an image segmentation procedure that identifies and segments one or more anatomical features in an image, the method comprising:
   obtaining different image segmentations of two or more images of an anatomical region of a patient, representative of the anatomical region at different respective time points, wherein each of the two or more images is segmented using the image segmentation procedure;
   determining one or more measures of consistency between the different image segmentations based on a comparison of the different image segmentations; and
   determining a measure of accuracy of the image segmentation procedure based on the one or more measures of consistency and on reference to a pre-determined normal degree of inconsistency between the different image segmentations of the two or more images,
   wherein the one or more measures of consistency are distinct from the measure of accuracy,
   wherein the pre-determined normal degree of inconsistency is representative of expected variations or movement of the anatomical region at the different respective time points, and
   wherein the different respective time points correspond to defined time points in a periodic or cyclic movement pattern of the anatomical region.

2. The method as claimed in claim 1, wherein determining the one or more measures of consistency comprises comparing one or more similar segmented features, segmented in each of the different image segmentations, and determining the one or more measures of consistency between the one or more similar segmented features in the different image segmentations.

3. The method as claimed in claim 2, wherein determining the one or more measures of consistency comprises comparing at least one of a position, a shape, or one or more dimensions of at least a portion of the different image segmentations.

4. The method as claimed in claim 1, wherein the measure of accuracy is further based on applying one or more pre-determined minimum thresholds for the one or more measures of consistency.

5. The method as claimed in claim 1, wherein at least one of determining the one or more measures of consistency or determining the measure of accuracy comprises use of a machine learning algorithm.

6. The method as claimed in claim 5, wherein determining the measure of accuracy comprises use of a machine learning algorithm, and
   wherein the machine learning algorithm is trained for distinguishing between normal and abnormal levels of inconsistency between image segmentations of the anatomical region at different time points.

7. The method as claimed in claim 5, wherein both determining the one or more measures of consistency and determining the measure of accuracy comprise use of a machine learning algorithm.

8. The method as claimed in claim 1, wherein the measure of accuracy comprises a probabilistic measure of accuracy.

9. The method as claimed in claim 1, wherein the method is performed in real time with obtaining of the different image segmentations.

10. The method as claimed in claim 1, wherein the method is an ultrasound image analysis method such that the two or more images of the anatomical region are ultrasound images.

11. The method as claimed in claim 1, wherein the obtaining of the different image segmentations comprises:
    receiving the two or more images of the anatomical region; and
    processing the two or more images with the image segmentation procedure.

12. The method as claimed in claim 1, wherein obtaining the one or more image segmentations comprises:
    receiving ultrasound data;
    processing the ultrasound data to derive the two or more images of the anatomical region, representative of the anatomical region at different respective time points; and
    processing the derived two or more images with the image segmentation procedure.

13. The method as claimed in claim 1, wherein the measure the accuracy is configured to indicate whether a variation in the one or more measures of consistency is representative of:
    the failures in the image segmentation procedure; or
    natural movement of the anatomical region.

14. The method as claimed in claim 1, further comprising outputting a first representation of the measure of accuracy to a display.

15. The method as claimed in claim 14, further comprising outputting a second representation of a recommendation for changing acquisition of images of the anatomical region.

16. The method as claimed in claim 1,
    wherein, when the measure of accuracy for the different image segmentations is unacceptable, at least one of the two or more images of the anatomical region are not output to a display, and
    wherein, when the measure of accuracy for the different image segmentations is acceptable, the two or more images of the anatomical region are output to a display.

17. An image analysis device for determining failures in an image segmentation procedure that identifies and segments one or more anatomical features in an image, the image analysis device comprising:

an acquisition module configured to obtain different image segmentations of two or more images of an anatomical region of a patient, representative of the anatomical region at different respective time points, wherein each of the two or more images is segmented using the image segmentation procedure, wherein the different respective time points correspond to defined time points in a periodic or cyclic movement pattern of the anatomical region;

a comparison module configured to determine a measure of consistency between the different image segmentations based on a comparison of the different image segmentations; and an analysis module configured to determine a measure of accuracy of the image segmentation procedure based on the measure of consistency and on reference to a pre-determined normal degree of inconsistency between the different image segmentations of the two or more images, wherein the measure of consistency is distinct from the measure of accuracy, and wherein the pre-determined normal degree of inconsistency is representative of expected variations or movement of the anatomical region at the different respective time points.

18. An ultrasound system, comprising:

an ultrasound transducer unit; and the image analysis device as claimed in claim 17, operatively coupled with the ultrasound transducer unit for use in obtaining different image segmentations.

19. An image analysis device for determining failures in an image segmentation procedure that identifies and segments one or more anatomical features in an image, the image analysis device comprising:

one or more processors; and one or more non-transitory storage media storing instructions that, when executed by the one or more processors, cause the one or more processors to:

receive two or more images of an anatomical region of a patient representative of the anatomical region at different respective time points;

perform image segmentation of the two or more images using the image segmentation procedure to provide different image segmentations of the two or more images, wherein the different respective time points correspond to defined time points in a periodic or cyclic movement pattern of the anatomical region;

determine a measure of consistency between the different image segmentations based on a comparison of the different image segmentations; and determine a measure of accuracy of the image segmentation procedure based on the measure of consistency and on reference to a pre-determined normal degree of inconsistency between the different image segmentations of the two or more images, wherein the measure of consistency is distinct from the measure of accuracy, and wherein the pre-determined normal degree of inconsistency is representative of expected variations or movement of the anatomical region at the different respective time points.

20. The image analysis device as claimed in claim 19, wherein determining the measure of consistency comprises comparing one or more similar segmented features, segmented in each of the different image segmentations, and determining the measure of consistency between the one or more similar segmented features in the different image segmentations.

* * * * *